United States Patent [19]

Larson

[11] 4,230,127
[45] Oct. 28, 1980

[54] CARDIAC MONITORING APPARATUS

[75] Inventor: Lary R. Larson, Tempe, Ariz.

[73] Assignee: Medtronic, Inc., Minneapolis, Minn.

[21] Appl. No.: 909,230

[22] Filed: May 24, 1978

[51] Int. Cl.³ ............................................. A61B 5/04
[52] U.S. Cl. ................................. 128/706; 128/690;
128/639; 128/644
[58] Field of Search ...................... 128/2.05 T, 2.06 F,
128/2.06 R, 2.06 E, 2.1 E, 706, 690, 639-644

[56] References Cited
U.S. PATENT DOCUMENTS

| | | | |
|---|---|---|---|
| 3,568,662 | 3/1971 | Everett et al. ................... | 128/2.06 E |
| 3,606,881 | 9/1971 | Woodson ......................... | 128/2.06 E |
| 3,628,527 | 12/1971 | West ................................ | 128/2.06 E |
| 3,863,626 | 2/1975 | Huber .............................. | 128/2.05 T |
| 3,924,639 | 12/1975 | Hess ................................ | 128/419 P |
| 4,033,355 | 7/1977 | Amundson ....................... | 128/419 P |
| 4,120,294 | 10/1978 | Wolfe .............................. | 128/2.05 T |

FOREIGN PATENT DOCUMENTS

| | | | |
|---|---|---|---|
| 2309467 | 8/1974 | Fed. Rep. of Germany ...... | 128/2.06 F |
| 2736751 | 2/1978 | Fed. Rep. of Germany ...... | 128/2.05 T |

OTHER PUBLICATIONS

Miller, H. A. et al., "Biomedical Electrode Technology Theory & Practice," Academic Press Inc., 1974, pp. 5-93.

*Primary Examiner*—Robert W. Michell
*Assistant Examiner*—Francis J. Jaworski
*Attorney, Agent, or Firm*—Lew Schwartz; Joseph F. Breimayer; Carl A. Forest

[57] ABSTRACT

There is disclosed herein a wristwatch size cardiac monitoring apparatus which is worn on the wrist of one arm. A conductive material housing acts as one electrode when held firmly in contact with the wrist of the arm on which it is worn. A finger of the other limb is placed on a receiving electrode of the casing which acts as the second electrode. Together, these two electrodes provide a Lead I electrocardiac signal to electronics within the housing. The second electrode consists of a metal layer on which is placed a dielectric material and when the finger is placed on top of the dielectric material, a capacitor is formed and the electric signal on the finger is transferred to the metal layer. Additionally, there is described circuitry which is used to operate the rate monitor. This circuitry includes means for detecting a QRS complex and for causing a count in beats per minute to be displayed, manifesting the heartbeat rate. The circuitry includes means for updating the heartbeat rate displayed every two seconds and for automatically turning the system off when no heartbeats are detected for a six second interval.

4 Claims, 7 Drawing Figures

CARDIAC MONITORING APPARATUS

This invention relates to portable cardiac monitoring apparatus and, more particularly, to such apparatus adapted to be worn on the wrist of a user in which the back of the watch casing constitutes one input electrode and an electrode insulated from the casing placed on the front of the watch constitutes a second electrode, whereby a Lead I EKG signal can be derived.

In the prior art there exists a number of devices which are capable of being worn on the wrist of a user and monitoring his heartbeat rate. These devices fall into two classifications. One monitors the pulse rate of the wearer by either an acoustical, optical or pressure-sensitive transducer. The other type of unit is connected to skin electrodes which are attached to the person's body and monitors the electrocardiac signal to determine the heartbeat rate. This invention relates to the latter type of device, that is, the one which monitors the electrocardiac (EKG) signal and determines the heartbeat rate therefrom.

The problem with the EKG signal monitoring type devices has always been that it is necessary to provide wires from the device to electrodes attached to an appropriate point, generally on the chest, of the person using the device in order to derive the EKG signal. These wires and electrodes are a major cause of failure in the proper operation of the devices. Problems generally associated with the wire electrodes are that they dislodge, the conductive jelly used to attach the electrodes dries out, thereby causing inadequate or extremely noisy signals to be applied to the monitoring device, or the wires themselves break. One type of device which eliminates the need for the wires is described in U.S. Patent application Ser. No. 714,873 in the name of John M. Adams, now abandoned, which application is assigned to the present assignee hereof. In the Adams application two embodiments are shown for eliminating the need for the wires. The first embodiment utilizes a wristband, such as a commercially available expansion band utilized with a common wristwatch, on the two wrists of the user. When it is desired to take a cardiac rate, the user merely places the bands together so as to derive an EKG signal taken between the two arms, or in other words, a Lead I EKG signal. In the second embodiment the user merely grasps two electrodes on the sides of the watch, which side electrodes are insulated from the band or casing. In this manner the two side electrodes upon pressure being applied from the fingers detect a Lead I EKG signal. Problems have been encountered in attempting to derive signals from a percentage of the population with the above described Adams device because of poor pickup, which has been found to exist in the case of the metal receiving electrodes described therein. In addition, the placement of the side electrodes is cumbersome and they would be better placed on the face of the monitor.

One type of cardiac signal detecting electrode which has been described in the prior art utilizes a capacitive input to receive the electric skin signals. Such capacitive electrodes include a metal material on to which is attached a dielectric material, adapted to be placed in physical contact with the body. When so placed, the body acts as one plate and the metal material as the second plate of a capacitor. The EKG signal on the skin is thus passed to the metal material from where it can be easily applied to the electric circuits. For a more detailed description of such an electrode reference should be made to the textbook entitled "Biomedical Electrode Technology Theory and Practice", edited by Harry A. Miller and Donald C. Harrison, Academic Press, Inc., 1974, and specifically Section 1 therein entitled "Material Sciences", Chairman Allan Pinkerson, M.D. The devices described in this reference relate to electrodes designed to be utilized as permanent fixtures attached to the body, such as are commonly used with electrocardiograph machines and with the prior art wristwatch size portable EKG rate monitors.

Other problems which exist in prior art wristwatch size cardiac rate monitors are found in the circuitry for processing the detected cardiac signals. Typical of the circuits of these devices is the one described in the above-referenced Adams application. These include counting the number of pulses over a defined time interval of, for instance, six seconds and then displaying ten times the number counted during the six second interval so that the displayed count is in beat per minute terms. This type of displaying system is accurate to only the tens significant digit; thus, a person with a heartbeat rate of 77 beats per minute may have a rate of either 70 or 80 displayed. Also, with this type of circuitry, it is difficult to continually update a preexisting average rate with new data so that one is displaying an average rate over a period of time rather than the number of beats during a six second time interval.

Another feature which is not shown or described in the prior art is circuitry for automatically turning off the rate monitor whenever no beats are detected for a certain time. Typically, the monitor must be manually turned off by the depression of a switch means. In many instances, the user may forget to operate the switch to turn off the device, and thus the device continues drawing durrent from the battery powering it. This, of course, causes the battery to become depleted and the device to then be inoperative until such time as a new battery may be inserted.

According to one aspect of this invention there is provided on a portable cardiac rate monitor adapted to be worn on one wrist and including case means for housing electrical means capable of detecting a Lead I electrocardiac signal in response to the electrical signals taken between two upper limbs in which the case means includes a conductive back which is adapted to be in physical contact with one of the limbs and receives one of the electrical signals for provision to the electrical means. The improvement herein is receiving means on the case for providing the other electrical signal to the electrical means which comprises a conductive layer insulated from the backing and a dielectric layer affixed to the conductive layer on the side thereof remote from the case and adapted to have a part of the other limb placed in physical contact therewith.

A preferred embodiment of the present invention is hereafter described with specific reference being made to the following FIGURES, in which.

Figure 4A:
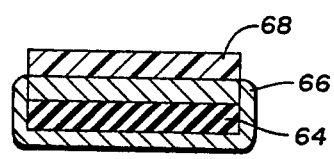
Figure 4B:
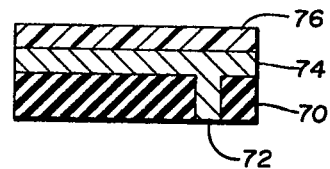
Figure 4C:
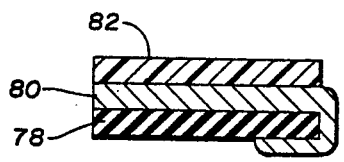
Figure 2:
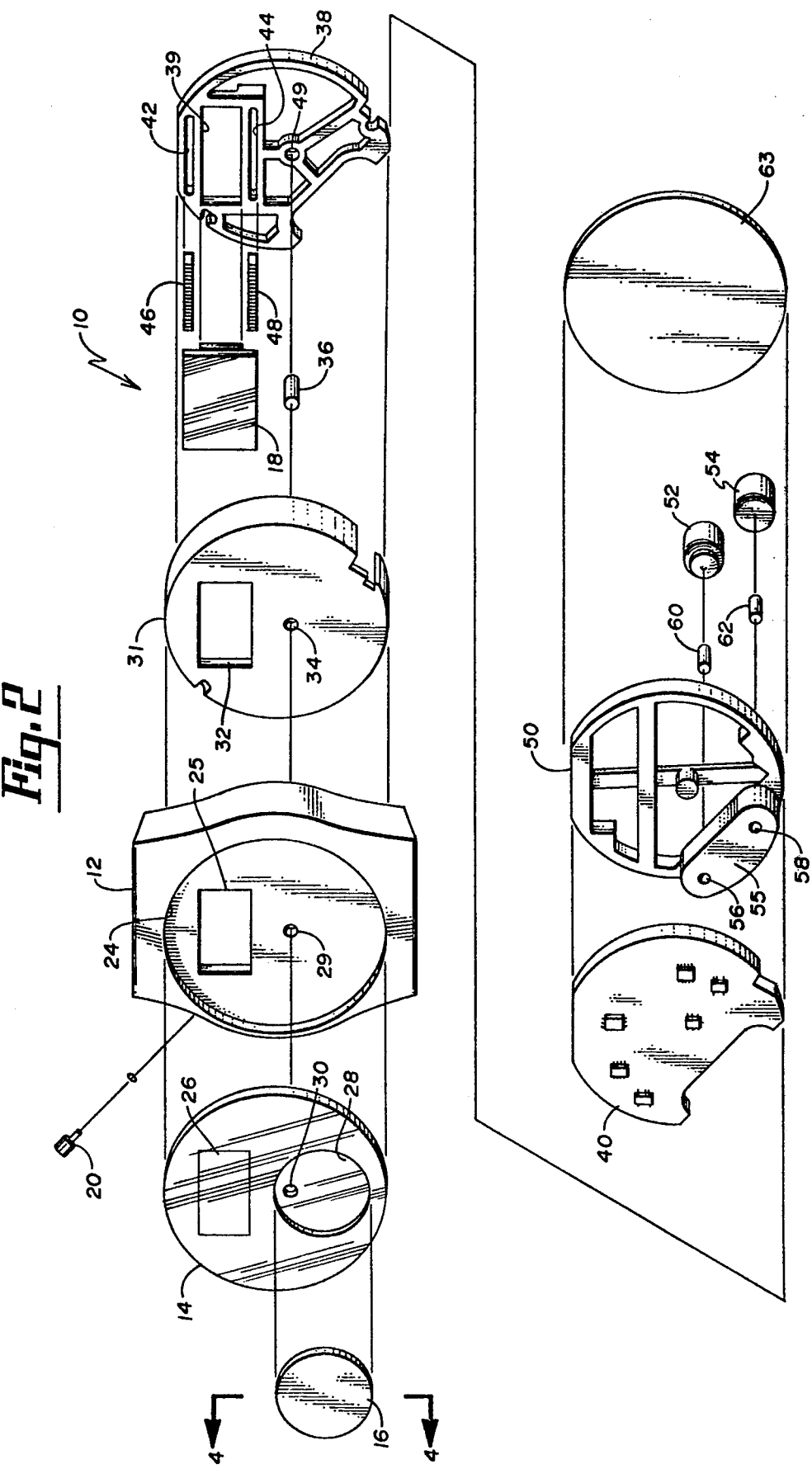
FIG. 2 is an exploded view from one direction of the various components assembled to form the portion other than the band of the rate monitor shown in FIG. 1.
Figure 5:
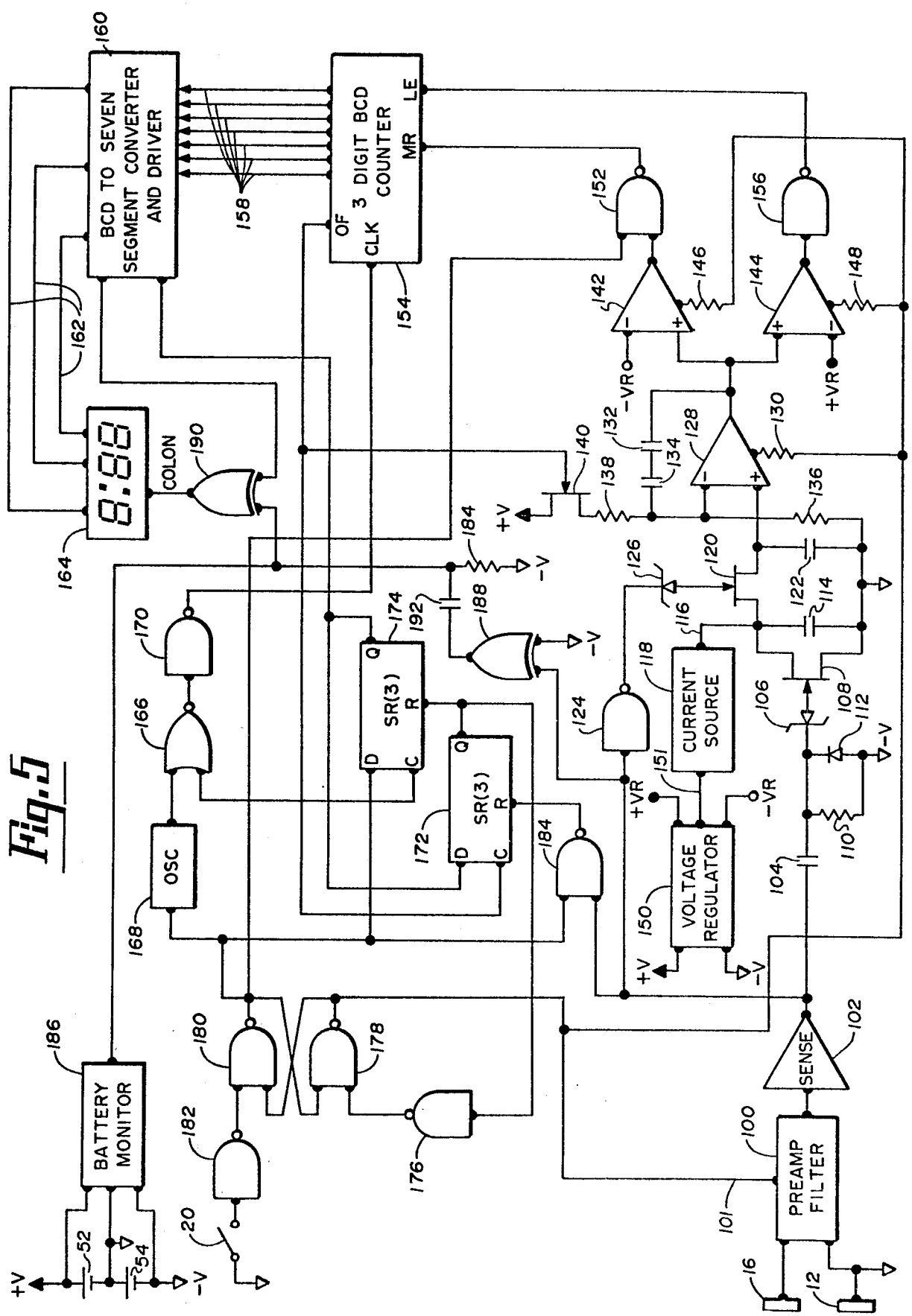

FIGS. 4A, 4B and 4C respectively show, in cross section, three different embodiment of receiving electrodes in a view taken across Line 4—4 of FIG. 2; and FIG. 5 is a schematic electrical diagram showing the electrical circuit used with the rate monitor of this invention.

Figure 1:
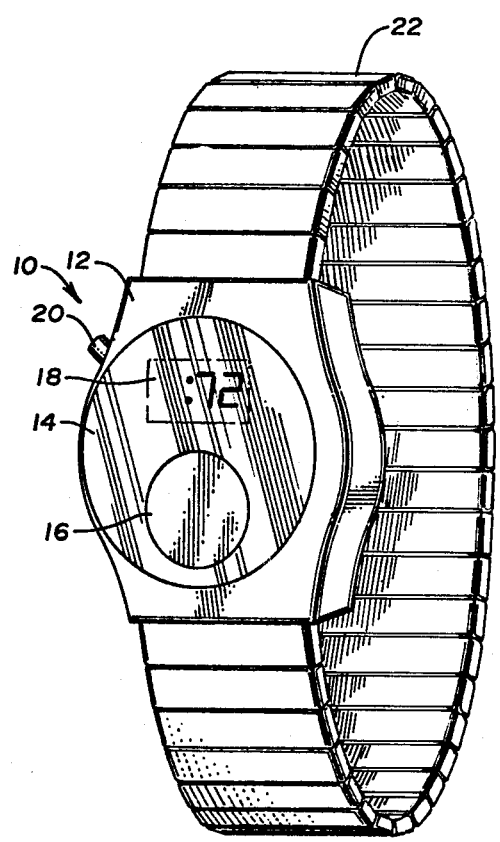
FIG. 1 shows a rate monitor in accordance with the present invention.

Referring now to FIG. 1, wrist rate monitor 10 is shown and includes a casing 12 which may be of a conductive material such as stainless steel having a faceplate 14, which may be of a material such as mineral glass that is silkscreened with a paint on the rear surface, and inserted therein. Faceplate 14 has inserted therein an electrode 16 which will be described in more detail with respect to FIGS. 4A, 4B and 4C. In addition, on faceplate 14 there is a clear opening for a display 18, such as commercially available liquid crystal displays or light emitting diode displays. Housing 12 also includes an on-off switch 20 which is to be depressed and spring released each time it is desirous to turn on rate monitor 10. Finally, rate monitor 10 includes a conventional expansion watchband 22 attached in a manner similar to the way one is attached to a conventional wristwatch. The purpose of watchband 22 is to hold casing 12 firmly in contact with the wrist in order to get an electrical signal provided thereto as one part of a Lead I EKG signal.

As is well known in the art, a Lead I EKG signal is a signal taken generally horizontally across the heart. This signal is conventionally derived by looking at the difference in signals taken between the two arms of the subject. Conventionally the signals are derived from the wrist area of the arm although they could be derived from any area, such as the shoulders or the fingers. In monitor 10, the Lead I EKG is taken between the wrist of one arm and a finger of the other arm by casing 12 being held by band 22 in contact with the wrist of one arm and the user placing a finger from the other arm in contact with electrode 16. As will be described in more detail hereafter, electrode 16 is a capacitive type electrode which includes a layer of conductive material, such as silver, and a layer of dielectric material, such as the Product Number 8289 (consisting of a platinum, gold and silicon dioxide mixture) manufactured by the DuPont Company of Wilmington, Del. The dielectric material is facing the outside of monitor 10 and covers the conductive material. Both of these materials may be attached to a ceramic substrate for physical strength and an electrical connection is provided between the conductive material and the electronic components within housing 12. When a finger is placed on the dielectric material of receiving means 16 a capacitor is formed with the finger being one plate and the conductive material being the second plate. The voltage on the skin of the finger is transferred through the dielectric material to the other plate of the capacitor and from there to the electrical components of the circuit, where the heart rate is determined and displayed on display 18.

Figure 3:
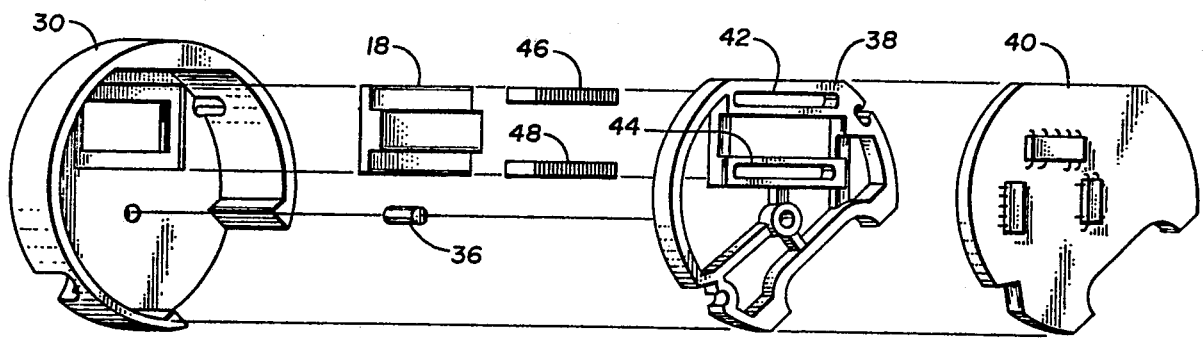
FIG. 3 is an exploded view from the other side of selected elements shown in FIG. 2.

Referring now to FIGS. 2 and 3, there is shown, in exploded view, monitor 10. Housing 12 which may be of a conductive material such as stainless steel, has a general shape of a commercial wristwatch. It includes a recess 24 into which is placed mineral glass 14. Mineral glass 14 may be silkscreened on the reverse side thereof with a paint to give it an appropriately pleasing color. However, an area 26 of mineral glass 14 is left clear in order that the display may be seen. In addition, an area 28 is etched in mineral glass 14 in order to receive electrode 16. Etch area 28 includes a hole 30 therein through glass 14 in order that electrical contact may be made with the conductive layer of electrode 16 and the remainder of the electronic circuitry. Electrode 16 is then placed in the etched area 28 of glass 14. Housing 12 also has a hole 29 in alignment with hole 30 and a square opening 25 in alignment with clear area 26.

In addition, on-off switch 20, which is a conventional pushbutton momentary relay closing switch is attached to one side of casing 12.

Inserted into the rear portion of housing 12 is a plastic member 31 having a rectangular opening 32 therein which is in alignment with openings 25 and 26 through which the display element 18 is to be inserted. In addition, a hole 34 is included in plastic member 31 which is in alignment with holes 29 and 30, through which a conductive rubber connector member 36 is placed so as to be in contact with the conductive layer of electrode 16.

Inserted next to member 31 is a plastic member 38 which holds the display member 18 in rectangular opening 39, which is in alignment with openings 25, 26 and 32. Electrical contact is provided from the output pads on display 18 to component holder 40 through holes 42 and 44 in element 38 by the use of two zebra connector devices 46 and 48. These devices are well known in the art and consist of alternating conductor insulator layers such that conduction is provided in the vertical direction shown in FIG. 2 from pads on the bottom end of display member 18 to corresponding pads on component holder 40. In addition, there is provided a hole 49 in alignment with holes 29, 30 and 34 through which conductive rubber member 36 fits to electrically connect the conductive layer of electrode 16 to a pad on component holder 40.

Component holder 40 may be a ceramic element of an appropriate shape to fit behind component holder 38 and contains a variety of electrical components which have only been generally drawn in for illustrative purposes. It should be noted that the electrical pads on component holder 40 must be positioned to be in alignment with the pads of display 18. Also a pad must be provided which makes contact with conductive rubber member 36. On the other side of component holder 40 will be other components. Another plastic member 50 is placed in physical contact with component holder 40. Two batteries 52 and 54 are then placed in battery holder 55, which includes a pair of holes 56 and 58, in member 50. Batteries 52 and 54 are electrically connected to component holder 40 by conductive rubber members 60 and 62 inserted through holes 56 and 58. Finally, a plate 63 of a highly conductive material, such as stainless steel, is positioned on the back of housing 12 to hold all of the components within housing 12, and to electrically connect the positive terminal of battery 54 to the negative terminal of battery 52. Plate 63 so connected is at a point of reference potential, such as system ground, and acts as one of the two electrodes of monitor 10.

Referring now to FIGS. 4A, 4B and 4C, there is shown three different embodiments for electrode 16. In FIG. 4A, a substrate 64 has been dipped in a metal material, such as silver, to be entirely encased by a conductive layer such as palladium/silver. There is sputtered by conventional sputtering techniques, a layer of a dielectric material #4520, (consisting of a silicon oxide, lead oxide and sodium mixture) which may be purchased from the Electro-Science Laboratories, Inc., (hereinafter ELS 4520) on top of conductive layer 66.

When a finger is placed on top of layer 68 a capacitor is formed with conductive material 66 being one plate and the finger being the second plate of the capacitor and layer 68 being the dielectric material between the two plates. The electric signals from the heart appearing on the skin of the finger are transferred through dielectric material 68 to plate 66.

Referring again to FIG. 2, the conductive rubber member 36 is in firm compressed contact with the bottom portion of conductive material 66 when plate 63 is fit into casing 12 to provide an electric path from the plate formed of material 66 of the capacitor to the remaining portion of the electric circuitry on member 40 and shown schematically in FIG. 5.

In FIG 4B a substrate 70 is provided with a hole 72 therethrough. Placed on top of member 70 and through the hole 72 is a conductive layer 74 which may be silver metal. Again a dielectric material layer 76 is sputtered on top of layer 74. The operation of the electrode shown in FIG. 4B is the same as that shown in FIG. 4A, except that conductive rubber member 36 is compressed against the bottom of hole 72 which has been filled with the silver conductive material.

Referring now to FIG. 4C, a third type of electrode 16 is shown, which includes a substrate 78 of ceramic material which has had affixed thereto a layer 80 of a conductive material such as silver. Conductive layer 80 is continued, at least as a strip around the side to cover a portion of the bottom of substrate 78. Substrate 78 is then positioned so that conductive rubber member 36 makes contact therewith. Applied over the top of layer 80 is a dielectric material 82 of the same type previously described. Again, the operation of FIG. 4C is identical to that described with respect to FIG. 4A.

Referring now to FIG. 5, there is shown an electrical schematic diagram of the circuitry used in operating monitor 10. The input signals applied from finger electrode 16 and case 12 are applied to inputs of a preamp and filter circuit 100 which amplifies the approximately 0.5 Mv signal received and filters out muscle noise and other electrical noise which may be superimposed on the detected EKG signal. Circuit 100 includes conventional preamp and filter circuits utilizing operational amplifiers with appropriate biasing and feedback. The biasing circuits may be reversed bias by a negative voltage signal applied to line 101 so that circuit 100 draws virtually no current during the time monitor 10 is not in use. Characteristics of the filter portion of the circuit are a center frequency of approximately 20 Hz and a center frequency gain of approximately 3.6. The band pass filter reduces muscle artifact above and below the center frequency and in addition reduces 60 Hz interference.

The output from the preamp and filter circuit 100 is applied to a conventional cardiac signal detecting amplifier. Such an amplifier may be of a type conventionally used in a cardiac pacemaker. One such acceptable amplifier is described in U.S. Pat. No. 4,059,116. In addition to amplifying the signal, sense amplifier 102 provides other functions such as the rejection of continuous sine wave signals. The output pulse from sense amplifier 102 is a negative-going 2 msec. wide pulse which is provided each time a QRS complex of the EKG signal is detected.

Following the provision of the output pulse from sense amplifier 102, sense amplifier 102 causes itself to be immune from receiving any subsequent signals for a period of approximately 300 msec. This is similar to the refractory period which is well known in the cardiac pacing sense amplifier art. The reason for this, of course, is that the EKG signal includes several other waves following the QRS wave which should not be detected as additional heartbeat waves.

The output of sense amplifier 102 is connected to one end of a capacitor 104, the other end of which is connected to the cathode end of a zener diode 106. The anode end of diode 106 is connected to the gate of N channel junction field effect transistor 108. The junction between capacitor 104 and diode 106 is connected to one end of a resistor 110 and to the cathode end of a diode 112. The other end of resistor 110 and the anode end of diode 112 are connected together and to a source of negative voltage $-V$.

The emitter and collector of transistor 108 are connected across a capacitor 114. One end of capacitor 114 is connected to point of reference voltage, such as ground, and the other end to capacitor 114 has applied thereto, over line 116, a constant current $i_c$, which is provided from constant current source 118. Current source 118 may be a conventional voltage controlled constant current source well known in the art. Current $i_c$ may be selected to be 100 nAmp and the controlling voltage may be 1.2 volts above the lowest battery voltage $-V$.

The junction between transistor 108, capacitor 114 and line 116 is connected to one of the emitter and collector of an N channel junction field effect transistor 120. The other main electrode of transistor 120 is connected to one end of a capacitor 122, the other end of which is connected to ground. The output from sense amplifier 102 is connected through an inverter 124 and the cathode-anode path of a zener diode 126 to the base of transistor 120.

The operation of this portion of FIG. 5 is described hereafter. Between the time successive QRS complexes of the EKG signal are detected, capacitor 114 is charging up and storing an increasing voltage due to the application thereto of current $i_c$ over line 116. When a QRS complex of the EKG signal is detected, the output of sense amplifier 102 goes to a voltage approximately equal to $-V$ volts from a voltage previously at approximately $+V$. When this happens, transistor 120 is rendered conductive by the output from sense amplifier 102 through inverter 124 and the zener diode 126. This condition remains for the 2 msec. during which the pulse from sense amplifier 102 is provided. During this time, the voltage on capacitor 114 is applied through transistor 120 to capacitor 122. After this occurs a number of times, the voltage across capacitor 122 will manifest the average value of the rate of the heartbeat.

During the 2 msec. time that a pulse is provided at the output of sense amplifier 102, capacitor 104 charges up through diode 112 because the side of capacitor 104 remote from amplifier 102 was forced towards $-2$ V. After the end of the pulse from the amplifier 102, the voltage at the end of capacitor 104 remote from amplifier 102 will be sufficient to turn on transistor 108. This condition will remain for approximately 2 msec., which is the time determined by the discharge of capacitor 104 through resistor 110. While transistor 108 is turned on, capacitor 114 discharges through transistor 108 to ground. After transistor 108 is turned off by capacitor 104 discharging sufficiently, capacitor 114 again begins charging due to the current $i_c$ on line 116.

The junction of transistor 120 and capacitor 122 is applied to the noninverting input of an operational amplifier 128. Operational amplifier 128 additionally has applied thereto a source of bias voltage through resistor 130. The output of operational amplifier 128 is connected through serially connected capacitors 132 and 134 to the inverting input of operational amplifier 128. Capacitors 132 and 134 are oppositely poled polarized capacitors in order to have the effect of a single nonpolarized capacitor. The junction between capacitor 134 and the inverting input of amplifier 128 is connected through resistor 136 to ground. In addition, that junction is also connected through resistor 138 and the main electrodes of N channel junction field effect transistor 140 to source of positive voltage +V.

Connected in this manner, operational amplifier 128, capacitors 132 and 134 and resistor 136 form an integrating circuit. Thus, the output from amplifier 128 is a ramp voltage, which is the integral of the voltage appearing across capacitor 122.

The output of amplifier 128 is connected to the noninverting inputs of operational amplifiers 142 and 144. Each of amplifiers 142 and 144 have a biased voltage applied thereto through respective resistors 146 and 148. The inverting input of amplifier 142 is connected to a source of low reference voltage $-V_R$ volts and the inverting input of amplifier 144 is connected to a source of high reference voltage $+V_R$ volts. Each of these voltages $-V_R$ and $+V_R$ are provided from voltage reference source 150, which also provides a control voltage to current source 118 over line 151. The relative value of reference voltage $-V_R$ is greater than the voltage at which operational amplifier 128 provides voltage immediately after reset. In addition, the relative value of voltage $+V_R$ is less than the maximum magnitude reached by the voltage ramp provided from operational amplifier 128. The control voltage to current source 118 equals and tracks the absolute difference between $+V_R$ and $-V_R$.

The output from operational amplifier 142 is provided to one input of the two input NAND gate 152. The other input of NAND gate 152 is a signal which is high during normal operation of the circuit, but after automatic shutdown becomes low to thereby disable the passage of any signals through gate 152. The output of gate 152 is applied to the master reset (MR) of a three-digit binary coded decimal (BCD) counter 154. Whenever the output of gate 152 goes to a logic "0" or low level, counter 154 is enabled to count the pulses applied to the clock (CLK) input thereof.

The output from operational amplifier 144 is applied through inverter 156 to the latch enable (LE) input of counter 154. A single negative going pulse signal applied to the latch enable input of counter 154 causes signals to appear on the output lines 158 of counter 154, which signals manifests the count of counter 154 at the time the signal was applied through inverter 156 to the latch enable input. The signals on lines 158 continue to appear until another signal is applied to the latch enable input of counter 154. Lines 158 are applied to corresponding inputs of a binary coded decimal (BCD) to seven segment converter and driver circuit 160, which in turn supplies signals on lines 162 to a liquid crystal display 164. In this manner, the count which was latched in counter 154 by the signal through inverter 156 is converted and displayed at display 164. As will be explained in detail hereafter, this count is equal to the beat per minute heartbeat rate of the person utilizing rate monitor 10.

Counter 154 continues counting after a signal is applied to the latch enable input thereof, until it reaches a full count. The frequency of the clock providing the clock signals, the clock input of counter 154 and the maximum count of counter 154 are preselected so that counter 154 reaches a full count after a preselected update time, which may be approximately two seconds. For instance, the frequency of the clock signal may be 500 Hz and the maximum count of counter 154 may be 1000. When counter 154 reaches a full count, a signal appears at the overflow (OF) output thereof. This signal is applied to the base of transistor 140 to render it conductive. This causes a high voltage to be applied to the inverting input of operational amplifier 128, which in turn causes the output thereof to go low. When the OF signal is removed, transistor 140 turns off and capacitors 132 and 134 begin charging, thereby raising the voltage at the inverting input of amplifier 128 causing the voltage at its output to begin increasing in a linear ramp fashion.

During the time when the voltage at the output of operational amplifier 128 is more positive than $-V_R$ volts, the output of operational amplifier 142 is high and thus the output from gate 152 is low. During this period of time, counter 154 remains in the overflow condition because the overflow output is additionally provided to one input of NOR gate 166. The other input of NOR gate 166 has applied thereto the output from oscillator 168 which provides pulses at a frequency of 500 Hz when enabled by a signal on the enable input thereof. The output of NOR gate 166 is provided to inverter 170 to the clock input of counter 154. Whenever counter 154 goes to the overflow state, NOR gate 166 is blocked from passing the oscillator pulses and counter 154 remains in the overflow stage until reset by a high signal applied to the master reset input.

As the voltage at the output of integrator amplifier 128 decreases below the $-V_R$ value, the output of amplifier 142 changes states, thereby causing the output of NAND gate 152 to become positive. This low-to-high swing at the output of NAND gate 152 causes counter 154 to be reset to a low count, thereby removing the signal from the overflow output thereof. This, in turn, removes the inhibition at gate 166 and clock pulses are again applied to counter 154. However, counter 154 cannot count upward because of the high signal applied to its reset input. As the voltage at the output of integrator amplifier 128 increases above the $-V_R$ value, the output of amplifier 142 changes state, thereby causing the output of NAND gate 152 to become low. This will remove the reset condition of counter 154, so it begins to count upwards.

As the output of amplifier 128 goes above $+V_R$ volts, the output of amplifier 144 changes states, as does the output at inverter 156 and the latch enable input of counter 154 again causes the signal to be latched to the output lines 158. This continues such that approximately every two seconds, the output lines 158 receive a new reading of the heartbeat.

As previously explained, the voltage on capacitor 122 is inversely proportional to the rate at which heartbeats are detected by sense amplifier 102. This voltage acts as a reference input to integrator 128 and as it varies the slope of the ramp voltage at the output of amplifier 128 also varies. Thus, the greater the heart rate, the less the voltage will be across the capacitor 122 and the smaller the slope will be of the ramp voltage at the output of amplifier 128. With a small slope, the time for the voltage to increase from $-V_R$ to $+V_R$ will be longer and hence the count in counter 154 will increase, manifesting the increased heart rate. In the case of a decreased rate, the time capacitor 114 is charged is longer and hence it will charge to a greater value. Hence, the voltage on capacitor 122 will be at a greater value and the slope of the ramp provided at the output of amplifier 128 will be greater. Thus, the time for the voltage to increase from $-V_R$ to $+V_R$ will be less and the count in counter 154 will be smaller, manifesting the decreased heart rate.

By proper selection of component values for resistor 136, capacitors 114, 132 and 134, voltages $+V_R$ and $-V_R$ current $i_c$ and the frequency fo of oscillator 168, the heart rate in beats per minute for a time $T_{SA}$ between successive heartbeats can be directly displayed according to the following conversion formula:

$$\text{COUNT} = \frac{1}{T_{SA}} \cdot \frac{fo \cdot R_{136} \cdot C_{114} \cdot (C_{132} + C_{134}) \cdot (+V_R - (-V_R))}{i_c \cdot C_{132} \cdot C_{134}}$$

In the above formula, it should be recalled that the control voltage applied from voltage regulator 150 over line 151 to control current $i_c$ from current source 18 is equal to and tracks the absolute difference between $+V_R$ and $-V_R$. Hence, one utilizes the expression $(+V_R-(-V_R))$ in place of the control voltage for $i_c$ in selecting the variables.

In order to make utilization of this equation, resistor 136 should be of a type which can be functionally trimmed during the manufacturing process from approximately 250 Kohms to a desired value of approximately 413 Kohm to compensate for other circuit parameter variables. The 413 Kohm value for resistor 136 assumes fo to be 500 Hz, capacitors 114, 132 and 134 to each be 0.22 microfarads, $(+V_R-(-V_R))$ to be 1.2 volts and $i_c$ to be 100 nanoamps.

The overflow output from counter 154 is additionally applied to the clock (C) input of two three-stage shift register circuits 172 and 174. In addition, each of shift registers 172 and 174 have a data (D) input and a reset (R) input and a Q output. Each time a signal is applied to the clock input of one of shift registers 172 and 174, the signal appearing at the data input is stored in the first stage thereof, the signal previously in the first stage is stored in the second stage and the signal previously stored in the second stage is stored in the third stage and appears as the signal at the Q output of the shift register.

The Q output from shift register 174 is coupled to the data (D) input of shift register 172 and additionally coupled to provide voltage to the BCD to seven segment converter and driver circuit 160. Until the Q output of shift register 174 goes high, there can be no display of a signal because no supply voltage is applied to BCD to seven segment converter and driver 160. The Q output from shift register 172 is applied to the reset input of shift register 174 and, in addition, through inverter 176 to one input of two input NAND gate 178. The output of NAND gate 178 is applied to one input of two input NAND gate 180, the output of which is applied back to the other input of NAND gate 178. The other input of NAND gate 180 receives a low, or logic "0", signal from inverter 182 each time the switch 20 of rate monitor 10 is momentarily depressed, thereby causing a high, or logic "1" signal to be provided to the input of inverter 182.

NAND gates 178 and 180 connected in a manner described constitute a conventionally set-reset latch circuit which becomes set whenever a low signal is applied from inverter 182 to gate 180 whereby the output of gate 180 becomes high and the output of gate 178 to be low. The low output from gate 178 is fed back to the input of NAND gate 180 to maintain it at a high state. Whenever a low signal is applied from the output of inverter 176, as a result of the Q output of shift register 172 going high, the output of NAND gate 178 is forced high, thereby forcing the output of NAND gate 180 low. This, in turn, maintains the output of NAND gate 178 high.

The output from NAND gate 178 is applied to control the bias of amplifiers 128, 142 and 144. This is done by applying the output from NAND gate 178 through respective resistors 130, 146 and 148. When the output of NAND gate 178 goes low, the amplifiers 128, 142 and 144 are allowed to operate. When the output of NAND gate 178 goes high, the biasing mechanisms within amplifiers 128, 142 and 144 are reverse biased and thus the amplifiers 128, 142 and 144 are shut down and draw negligible current. This is provided in order to save power when the rate monitor is not being used. In addition, the output from NAND gate 178 is coupled to line 101 to reverse bias the operational amplifiers included in preamp and filter circuit 100 in the same manner as just described with respect to amplifiers 128, 142 and 144.

The output from NAND gate 180 is applied as the second input to two input NAND gate 152 and enables NAND gate 152 to operate and pass signals to reset counter 154. At the time of shutdown of the circuit shown in FIG. 5, the output of NAND gate 180 goes low, which causes the output of NAND gate 152 to become high, thereby resetting counter 154.

The output of NAND gate 180 is also applied as the data input of shift register 174 and as one input to NAND gate 184. The other input of NAND gate 184 is the pulse provided at the output of sense amplifier 102. Thus, as long as the circuit is powered up, that is, NAND gate 180 is set and provides a high output, the output from NAND gate 184 will be high each time a pulse is detected, thereby resetting all the stages of shift register 172. In addition, the output of NAND gate 180 is applied to the enable input of oscillator 168 to enable it to provide pulses to counter 154 through gates 166 and 170.

In operation, the above described circuit components prevent a display from happening for six seconds after the switch 20 is depressed and signals begin appearing at the input of amplifier 102. At the time switch 20 is closed, the output of gate 180 goes high, counter 154 begins counting and approximately two seconds later, the first signal appears at the overflow output therefrom. This shifts the high value then appearing at the data input of shift register 174 into the first stage. It also shifts a low value into the first stage of shift register 172. After two seconds, a second overflow signal appears and shifts high values into both the first and second stages of shift register 174. After the third two second period, all three of the stages of shift register 174 will contain high values and the Q output of shift register 174 becomes a high value. This provides voltage to enable BCD to seven segment converter and driver circuit 160. This initial six second period is required in order to enable capacitor 122 to stabilize to the voltage to which capacitor 114 is charged and to maintain its value.

If for some reason the user of the device removes his finger from electrode 10, heartbeat signals will stop being applied through circuit 100 and detected by amplifier 120. During the period when heartbeats were continually detected, shift register 172 was continually reset by the output from gate 181 and the Q output thereof never achieved a high state. However, with removal of an applied cardiac signal, shift register 172 will now begin shifting high values therethrough and six seconds later the Q output thereof will attain a high state. This high state will be inverted by inverter 176 and reset the latch consisting of flip-flops 178 and 180, thereby causing the output of NAND gate 178 to go high and the output of NAND gate 180 to go low. When the output of NAND gate 178 goes high, the bias is removed and amplifiers and the circuit begins shutting down. Also at the time that shift register 172 goes high, shift register 174 is reset and power is removed from the BCD to seven segment driver 160.

A battery monitor circuit is also provided which monitors the battery voltage and provides a signal to the user whenever the battery begins wearing down. The battery monitor circuit additionally includes exclusive OR gates 188 and 190, each of which has two inputs and one output. Coupled to one input of exclusive OR gate 188 is the output of sense amplifier 102 with the other input of exclusive OR gate 188 coupled to a point of negative battery voltage $-V$. The output of exclusive OR gate 188 is coupled to capacitor 192 and resistor 194 to the point of negative battery voltage $-V$. The junction of capacitor 192 and resistor 194 is coupled to one input of exclusive OR gate 190. In addition, the output of battery monitor circuit 186 is coupled to that same input of gate 190. Battery monitor circuit 186 provides an open circuit as long as the battery voltage is above a proper level and a high signal whenever the battery voltage falls below that predetermined level. The other input of gate 190 is coupled to the back plane output of BCD to seven segment converter and driver 160 and back plane input of display 164. The output of exclusive OR gate 190 is coupled to the colon input of display 164. Whenever the signal from capacitor 192 to the input of exclusive OR gate 190 is low, the colon is eliminated and whenever it is high, the colon is not eliminated.

Exclusive OR gate 188 and capacitor 192 and resistor 194 connected as such constitute a monostable multivibrator which generates a pulse signal each time a signal is received from sense amplifier 102. This signal is passed through exclusive OR gate 190. Since the back plane output from converter and driver 160 is low and thus the colon is caused to blink each time a heartbeat is detected. The blinking of the colon indicates to the user that the battery is providing sufficient voltage for proper use.

In the event the battery monitor senses a low voltage, the input to exclusive OR gate 190 from the battery monitor circuit 186 is forced high and thus the output of exclusive OR gate 190 is out of phase with the other input. This in turn maintains the colon in a continuous display state and thus indicates to the user that the battery should be changed.

In the circuit described above, the following component values are utilized:
capacitor 104: 0.001 microfarads
diode 106: MZC 5.1A10
transistor 108: 2N4338
resistor 110: 2 Mohms
diode 112: IN914
capacitor 114: 0.22 microfarads
transistor 120: 2N4338
capacitor 122: 0.47 microfarads
inverter 124: MCC14572E
diode 126: MZC 5.1A10
amplifier 128: ICL8023C
resistor 130: 20 Mohms
capacitor 132: 0.22 microfarads
capacitor 134: 0.22 microfarads
resistor 136: approximately 250 Kohm (trimmed for frequency conversion)
resistor 138: 10 Kohms
transistor 140: 2N4338
amplifier 142: ICL8023C
amplifier 144: ICL8023C
resistor 0146: 1 Mohm
resistor 148: 1 Mohm
gate 152: MCC14011B
counter 154: MCC14553B
inverter 156: MCC14572
converter and driver 160: DF411
display 164: MCL154
NOR gate 166: MCC14572
gate 170: MCC14572
shift register 172: MCC14015B
shift register 174: MCC14015B
inverter 176: MC14572
gate 178: MCC14011B
gate 180: MCC14011B
gate 182: MCC14572
gate 184: MCC14011B
gate 188: MCC14070B
gate 190: MCC14070B
capacitor 192: 0.033 microfarads
resistor 194: 20 Mohm
$+V$: 1.5 volts
$-V$: $-1.5$ volts
$+V_R$: $+0.3$ volts
$-V_R$: $-0.9$ volts

What is claimed is:

1. In a portable cardiac rate monitor adapted to be worn on one wrist including case means for housing electrical means capable of detecting a Lead I electrocardiac signal in response to the electrical signals taken between two upper limbs, said case means including a conductive back, which is adapted to be in physical contact with one of said limbs and receiving one of said electrical signals for provision to said electrical means, the improvement of receiving means on said case for providing said other electrical signal to said electrical means comprising:

a conductive layer insulated from said backing;
   a dielectric layer affixed to said conductive layer on the side thereof remote from said case, and adapted to have a part of said other limb placed in physical contact therewith; and
   a conductive rubber means connecting said conductive layer and said electrical means.

2. The invention according to claim 1 and further comprising substrate means to which said conductive layer is affixed, and wherein said conductive layer has at least a portion of its surface exposed on two opposing sides of said substrate means and said conductive rubber means is in contact with said surface of said conductive layer which is exposed in the direction away from said dielectric layer.

3. The invention according to claim 1 wherein said conductive rubber means is held in compressed contact between said conductive layer and said electrical means.

4. The invention according to claim 3 wherein said conductive rubber means is a conductive rubber cylinder.

* * * * *

UNITED STATES PATENT AND TRADEMARK OFFICE
CERTIFICATE OF CORRECTION

PATENT NO. : 4,230,127
DATED : October 28, 1980
INVENTOR(S) : Lary R. Larson

It is certified that error appears in the above-identified patent and that said Letters Patent are hereby corrected as shown below:

Column 2,
    Line 38, "durrent" should be --current--;

Column 12,
    Line 19, "resistor 0146" should be --resistor 146--.

Signed and Sealed this

Twenty-fourth Day of March 1981

[SEAL]

Attest:

RENE D. TEGTMEYER

Attesting Officer     Acting Commissioner of Patents and Trademarks